United States Patent
Otts

(10) Patent No.: US 10,509,238 B2
(45) Date of Patent: Dec. 17, 2019

(54) ELECTROWETTING OPTHALMIC OPTICS INCLUDING GAS-PERMEABLE COMPONENTS

(71) Applicant: Verily Life Sciences LLC, Mountain View, CA (US)

(72) Inventor: Daniel Otts, Mountain View, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 241 days.

(21) Appl. No.: 15/488,338

(22) Filed: Apr. 14, 2017

(65) Prior Publication Data

US 2018/0299701 A1 Oct. 18, 2018

(51) Int. Cl.
*G02C 7/00* (2006.01)
*G02C 7/08* (2006.01)
(Continued)

(52) U.S. Cl.
CPC ............ *G02C 7/085* (2013.01); *A61F 2/1613* (2013.01); *A61F 2/16015* (2015.04);
(Continued)

(58) Field of Classification Search
CPC .......... G02C 7/085; G02C 7/04; G02C 7/045; G02C 7/049; G02C 7/083; G02C 7/022;
(Continued)

(56) References Cited

U.S. PATENT DOCUMENTS

| 8,513,324 B2 | 8/2013 | Scales et al. |
| 2005/0288196 A1 | 12/2005 | Horn |
| 2007/0153405 A1* | 7/2007 | Kuiper ..................... G02B 3/14 359/846 |

(Continued)

FOREIGN PATENT DOCUMENTS

| WO | 2004015460 A1 | 2/2004 |
| WO | 2005088388 A1 | 9/2005 |

(Continued)

OTHER PUBLICATIONS

International Search Report and Written Opinion from the International Searching Authority dated Jul. 5, 2018, for International Application No. PCT/US2018/023855, filed Mar. 22, 2018, 14 pages.

*Primary Examiner* — William R Alexander
*Assistant Examiner* — Henry A Duong
(74) *Attorney, Agent, or Firm* — Christensen O'Connor Johnson Kindness PLLC

(57) ABSTRACT

The disclosure describes an electrowetting contact lens comprising including an electrowetting cell. The cell includes first and second optical windows that form a sealed enclosure. A first electrode is formed on the first optical window, and a second electrode is formed on the second optical window. The first and second electrodes include an electrically conductive layer, and the first electrode includes at least one dielectric layer sandwiched between the relevant optical window and the at least one dielectric layer. Oil and saline layers are positioned in the sealed enclosure so that the oil is in contact with one electrode and the saline is in contact with the other electrode. A protective coating encloses the electrowetting cell, and a contact lens material encloses the sealing material. Other embodiments are disclosed and claimed.

29 Claims, 5 Drawing Sheets

(51) Int. Cl.
- *A61F 2/16* (2006.01)
- *B29D 11/00* (2006.01)
- *G02B 1/04* (2006.01)
- *G02C 7/04* (2006.01)
- *G02F 1/17* (2019.01)

(52) U.S. Cl.
CPC .. *B29D 11/00067* (2013.01); *B29D 11/00817* (2013.01); *G02B 1/043* (2013.01); *G02C 7/04* (2013.01); *G02C 7/045* (2013.01); *G02C 7/049* (2013.01); *G02C 7/083* (2013.01); *G02F 1/17* (2013.01); *A61F 2002/1699* (2015.04)

(58) Field of Classification Search
CPC ...... G02F 1/17; A61F 2/1613; A61F 2/16015; A61F 2002/1699; B29D 11/00067; B29D 11/00817; G02B 1/043
USPC ..................................................... 351/159.33
See application file for complete search history.

(56) References Cited

U.S. PATENT DOCUMENTS

| | | | |
|---|---|---|---|
| 2012/0026457 A1* | 2/2012 | Qiu | G02B 1/043 351/159.33 |
| 2012/0140167 A1* | 6/2012 | Blum | A61F 2/1624 351/159.34 |
| 2012/0200939 A1* | 8/2012 | Kuiper | G02B 26/005 359/665 |
| 2015/0286072 A1 | 10/2015 | Clarke | |
| 2015/0362754 A1 | 12/2015 | Etzkorn et al. | |
| 2016/0143728 A1 | 5/2016 | De Smet et al. | |
| 2017/0219825 A1* | 8/2017 | Benoit | G02B 27/0172 |

FOREIGN PATENT DOCUMENTS

| | | |
|---|---|---|
| WO | 2011042835 A1 | 4/2011 |
| WO | 2012061411 A1 | 5/2012 |
| WO | 2013096587 A1 | 6/2013 |
| WO | 2016025443 A1 | 2/2016 |
| WO | WO 2016/76523 | 5/2016 |

* cited by examiner

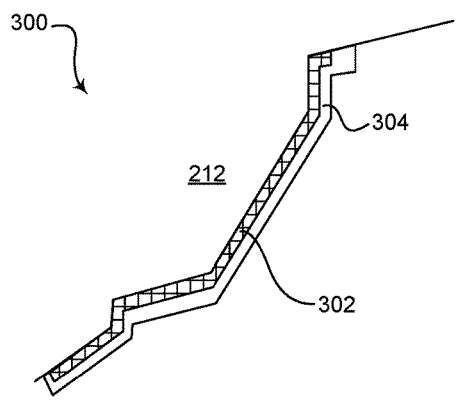
*Fig. 3*
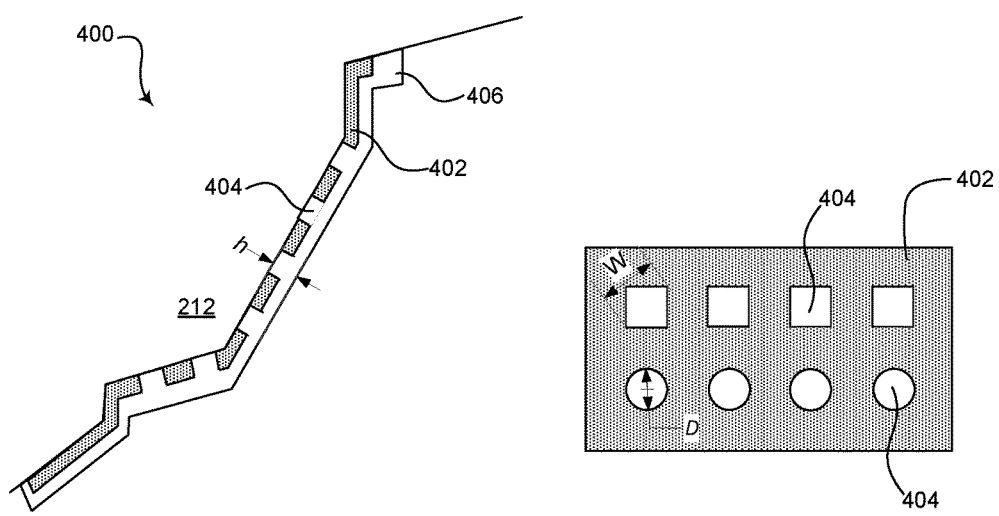
*Fig. 4A*  *Fig. 4B*

ELECTROWETTING OPTHALMIC OPTICS INCLUDING GAS-PERMEABLE COMPONENTS

TECHNICAL FIELD

The disclosed embodiments relate generally to ophthalmic optics and in particular, but not exclusively, to electrowetting ophthalmic optics, such as contact lenses, that include gas-permeable components.

BACKGROUND

Existing designs and methods for fabricating electrowetting lenses for ophthalmic applications (e.g., contact lenses) rely on gas-impermeable materials in their construction. For contact lens applications, all materials and/or devices positioned over the cornea should advantageously have good gas permeability, specifically oxygen permeability, due to the avascular nature of corneal tissues. Otherwise, the contact lenses could be uncomfortable and could lead to corneal edema and/or neovascularization.

BRIEF DESCRIPTION OF THE DRAWINGS

Non-limiting and non-exhaustive embodiments of the present invention are described with reference to the following figures, wherein like reference numerals refer to like parts in all the various views unless otherwise specified.

FIG. 2B is a cross-sectional view taken substantially along section line B-B in FIG. 2A.

FIG. 3 illustrates an embodiment of an oil electrode of the electrowetting cell.

FIGS. 4A-4B illustrate another embodiment of an oil electrode of the electrowetting cell.

DETAILED DESCRIPTION OF THE ILLUSTRATED EMBODIMENTS

Embodiments are described of an apparatus, system and method for electrowetting ophthalmic optics including gas-permeable constructions and components. Specific details are described to provide an understanding of the embodiments, but one skilled in the relevant art will recognize that the invention can be practiced without one or more of the described details or with other methods, components, materials, etc. In some instances, well-known structures, materials, or operations are not shown or described in detail but are nonetheless encompassed within the scope of the invention.

Reference throughout this specification to "one embodiment" or "an embodiment" means that a described feature, structure, or characteristic can be included in at least one described embodiment, so that appearances of "in one embodiment" or "in an embodiment" do not necessarily all refer to the same embodiment. Furthermore, the particular features, structures, or characteristics may be combined in any suitable manner in one or more embodiments.

Contact lenses with poor oxygen permeability provide an inferior patient experience due to discomfort, corneal edema, and corneal neovascularization over time. The advent of silicone hydrogel soft contact lens materials addressed this issue, and rigid gas-permeable contact lenses also addressed this issue, but to date no description of gas-permeable electrowetting lenses for contact lens applications exists. Without gas permeability, patients might not wear the lenses even if the electrowetting focusing technology provides a superior solution for their vision conditions, such as presbyopia. The described embodiments address the issue of oxygen impermeability in contact lens electrowetting optics by careful selection of gas-permeable materials and gas-permeable construction for use in improved designs of electrowetting optics.

Figure 1:
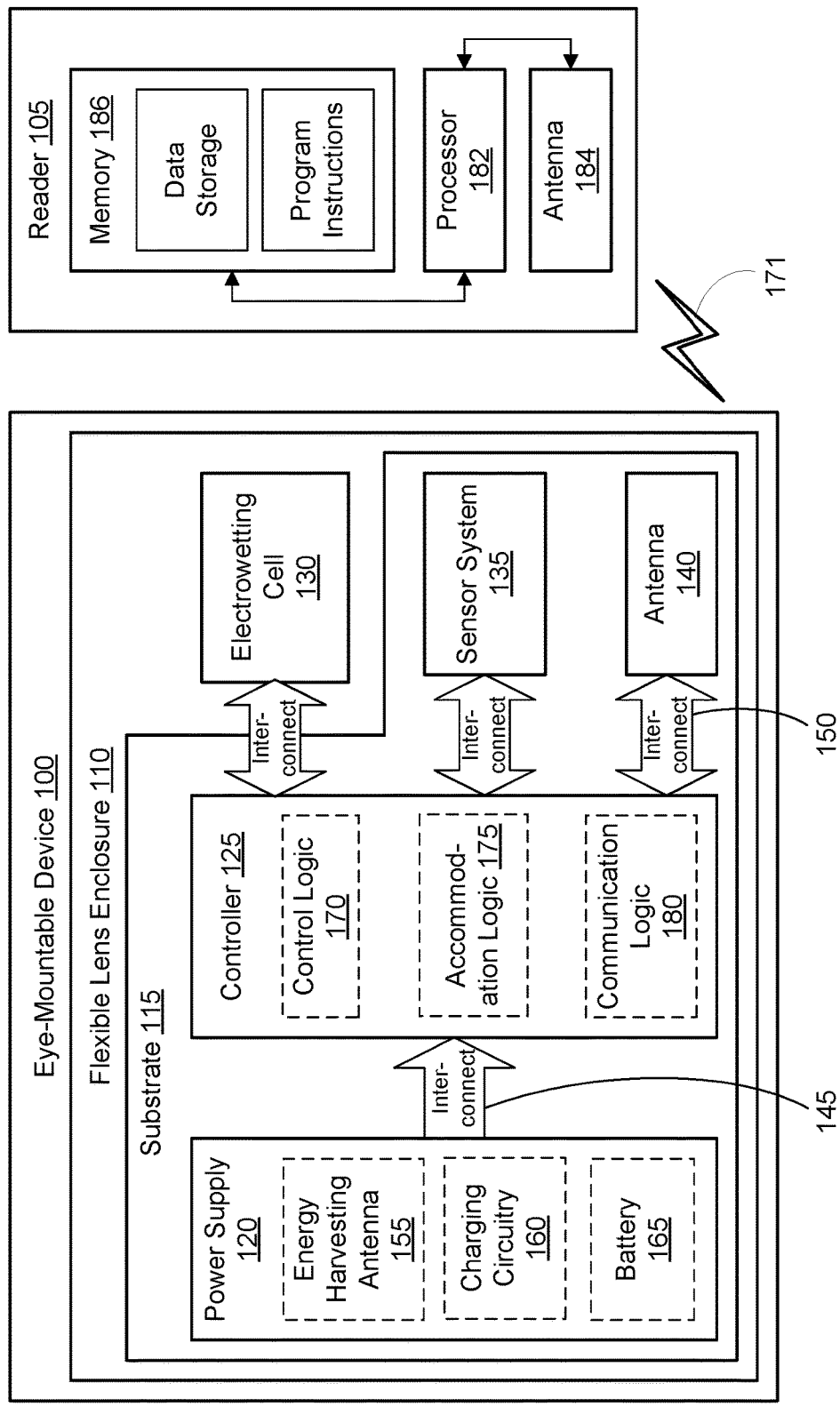
FIG. 1 is a functional block diagram of an embodiment of an eye-mountable device that provides auto-accommodation and an external reader for interacting with the eye-mountable device.

FIG. 1 illustrates, in block-diagram form, an embodiment of an eye-mountable device 100, in this case a gas-permeable electrowetting contact lens and an accompanying external reader 105. The exposed portion of eye-mountable device 100 is a flexible lens enclosure 110 formed to be contact-mounted to a corneal surface of an eye. A substrate 115 is embedded within or surrounded by flexible lens enclosure 110 to provide a mounting surface for a power supply 120, a controller 125, a sensor system 135, an antenna 140, and various interconnects 145 and 150. An electrowetting cell 130 is embedded within flexible lens enclosure 110 and coupled to controller 125 to provide auto-accommodation to the wearer of eye-mountable device 100. The illustrated embodiment of power supply 120 includes an energy harvesting antenna 155, charging circuitry 160, and a battery 165. The illustrated embodiment of controller 125 includes control logic 170, accommodation logic 175, and communication logic 180. The illustrated embodiment of reader 105 includes a processor 182, an antenna 184, and memory 186.

Controller 125 is coupled to receive feedback control signals from sensor system 135 and further coupled to operate electrowetting cell 130. Power supply 120 supplies operating voltages to the controller 125 and/or the electrowetting cell 130. Antenna 140 is operated by the controller 125 to communicate information to and/or from eye-mountable device 100. In one embodiment, antenna 140, controller 125, power supply 120, and sensor system 135 are all situated on embedded substrate 115. In one embodiment, electrowetting cell 130 is embedded within a center region of flexible lens enclosure 110, but is not disposed on substrate 115. Because eye-mountable device 100 includes electronics and is configured to be contact-mounted to an eye, it is also referred to herein as an ophthalmic electronics platform, a contact lens, or a smart contact lens.

To facilitate contact-mounting, the flexible lens enclosure 110 can have a concave surface configured to adhere ("mount") to a moistened corneal surface (e.g., by capillary forces with a tear film coating the corneal surface). Additionally, or alternatively, eye-mountable device 100 can be adhered by a vacuum force between the corneal surface and flexible lens enclosure 110 due to the concave curvature. While mounted with the concave surface against the eye, the outward-facing surface of flexible lens enclosure 110 can have a convex curvature that is formed to not interfere with eye-lid motion while the eye-mountable device 100 is mounted to the eye. For example, flexible lens enclosure 110 can be a substantially transparent curved disk shaped similarly to a contact lens.

Flexible lens enclosure 110 can include one or more biocompatible materials, such as those employed for use in contact lenses or other ophthalmic applications involving direct contact with the corneal surface. Flexible lens enclosure 110 can optionally be formed in part from such biocompatible materials or can include an outer coating with such biocompatible materials. Flexible lens enclosure 110 can include materials configured to moisturize the corneal surface, such as hydrogels and the like. Flexible lens enclosure 110 is a deformable ("non-rigid") material to enhance wearer comfort. In some instances, flexible lens enclosure 110 can be shaped to provide a predetermined, vision-correcting optical power, such as can be provided by a contact lens. Flexible lens enclosure 110 may be fabricated of various materials including a polymeric material, a hydrogel, PMMA, silicone based polymers (e.g., fluoro-silicon acrylate), or otherwise.

Substrate 115 includes one or more surfaces suitable for mounting sensor system 135, controller 125, power supply 120, and antenna 140. Substrate 115 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide or the flexible conductive materials discussed below) can be patterned on substrate 115 to form circuitry, electrodes, etc. For example, antenna 140 can be formed by depositing a pattern of gold or another conductive material on substrate 115. Similarly, interconnects 145 and 150 can be formed by depositing suitable patterns of conductive materials on substrate 115. A combination of resists, masks, and deposition techniques can be employed to pattern materials on substrate 115. Substrate 115 can be a relatively rigid material, such as polyethylene terephthalate ("PET") or another material sufficient to structurally support the circuitry and/or electronics within enclosure material 110. Eye-mountable device 100 can alternatively be arranged with a group of unconnected substrates rather than a single substrate. For example, controller 125 and power supply 120 can be mounted to one substrate, while antenna 140 and sensor system 135 are mounted to another substrate and the two can be electrically connected via interconnects.

Substrate 115 can be shaped as a flattened ring with a radial width dimension sufficient to provide a mounting platform for the embedded electronics components. Substrate 115 can have a thickness sufficiently small to allow the substrate to be embedded in flexible lens enclosure 110 without adversely influencing the profile of eye-mountable device 100. Substrate 115 can have a thickness sufficiently large to provide structural stability suitable for supporting the electronics mounted thereon. For example, substrate 115 can be shaped as a ring with a diameter of about 10 millimeters, a radial width of about 1 millimeter (e.g., an outer radius 1 millimeter larger than an inner radius), and a thickness of about 50 micrometers. Substrate 115 can optionally be aligned with the curvature of the eye-mounting surface of eye-mountable device 100 (e.g., convex surface). For example, substrate 115 can be shaped along the surface of an imaginary cone between two circular segments that define an inner radius and an outer radius. In such an example, the surface of substrate 115 along the surface of the imaginary cone defines an inclined surface that is approximately aligned with the curvature of the eye mounting surface at that radius.

In some embodiments, power supply 120 and controller 125 (and the substrate 115) can be positioned away from the center of eye-mountable device 100 to avoid interference with light transmission to the eye through the center of eye-mountable device 110. In contrast, electrowetting cell 130 can be centrally positioned to apply optical accommodation to the light transmitted to the eye through the center of eye-mountable device 110. For example, where eye-mountable device 100 is shaped as a concave-curved disk, substrate 115 can be embedded around the periphery (e.g., near the outer circumference) of the disk. In some embodiments, sensor system 135 includes one or more discrete capacitance sensors that are peripherally distributed to sense the eyelid overlap.

In the illustrated embodiment, power supply 120 includes a battery 165 to power the various embedded electronics, including controller 125. Battery 165 may be inductively charged by charging circuitry 160 and energy harvesting antenna 155. In one embodiment, antenna 140 and energy harvesting antenna 155 are independent antennae, which serve their respective functions of energy harvesting and communications. In another embodiment, energy harvesting antenna 155 and antenna 140 are the same physical antenna that are time shared for their respective functions of inductive charging and wireless communications with reader 105. Charging circuitry 160 may include a rectifier/regulator to condition the captured energy for charging battery 165 or directly power controller 125 without battery 165. Charging circuitry 160 may also include one or more energy storage devices to mitigate high frequency variations in energy harvesting antenna 155. For example, one or more energy storage devices (e.g., a capacitor, an inductor, etc.) can be connected to function as a low-pass filter.

Controller 125 contains logic to choreograph the operation of the other embedded components. Control logic 170 controls the general operation of eye-mountable device 100, including providing a logical user interface, power control functionality, etc. Accommodation logic 175 includes logic for monitoring feedback signals from sensor system 135, determining the current gaze direction or focal distance of the user, and manipulating electrowetting cell 130 in response to provide the appropriate accommodation. The auto-accommodation can be implemented in real-time based upon feedback from the gaze tracking, or permit user control to select specific accommodation regimes (e.g., near-field accommodation for reading, far-field accommodation for regular activities, etc.). Communication logic 180 provides communication protocols for wireless communication with reader 105 via antenna 140. In one embodiment, communication logic 180 provides backscatter communication via antenna 140 when in the presence of an electromagnetic field 171 output from reader 105. In one embodiment, communication logic 180 operates as a smart wireless radio-frequency identification ("RFID") tag that modulates the impedance of antenna 140 for backscatter wireless communications. The various logic modules of controller 125 can be implemented in software/firmware executed on a general-purpose microprocessor, in hardware (e.g., application specific integrated circuit), or a combination of both.

Eye-mountable device 100 can include various other embedded electronics and logic modules. For example, a light source or pixel array may be included to provide visible feedback to the user. An accelerometer or gyroscope may be included to provide positional, rotational, directional or acceleration feedback information to controller 125.

Figure 2A:
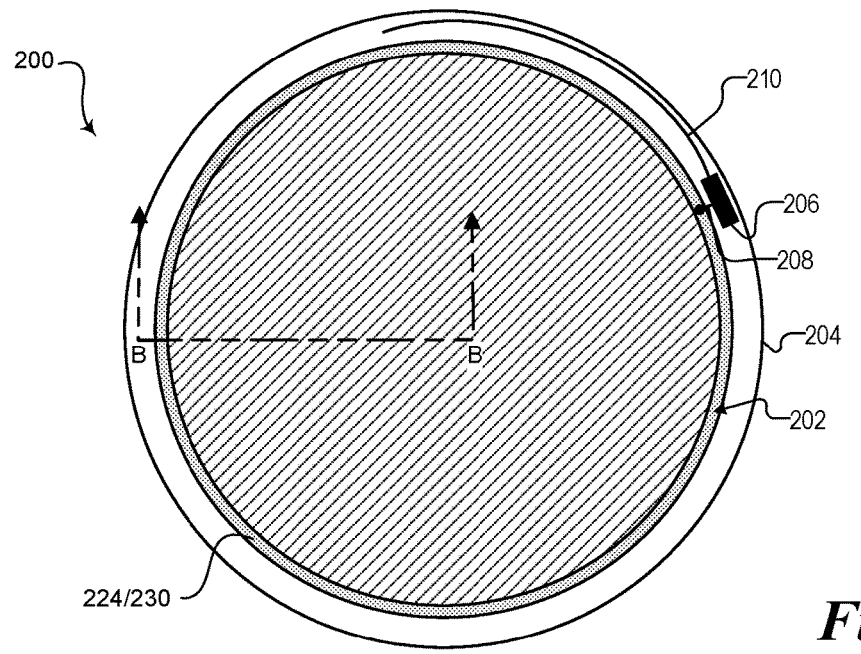
FIGS. 2A-2B together illustrate an embodiment of a gas-permeable contact lens including an electrowetting cell to provide accommodation.
Figure 2B:
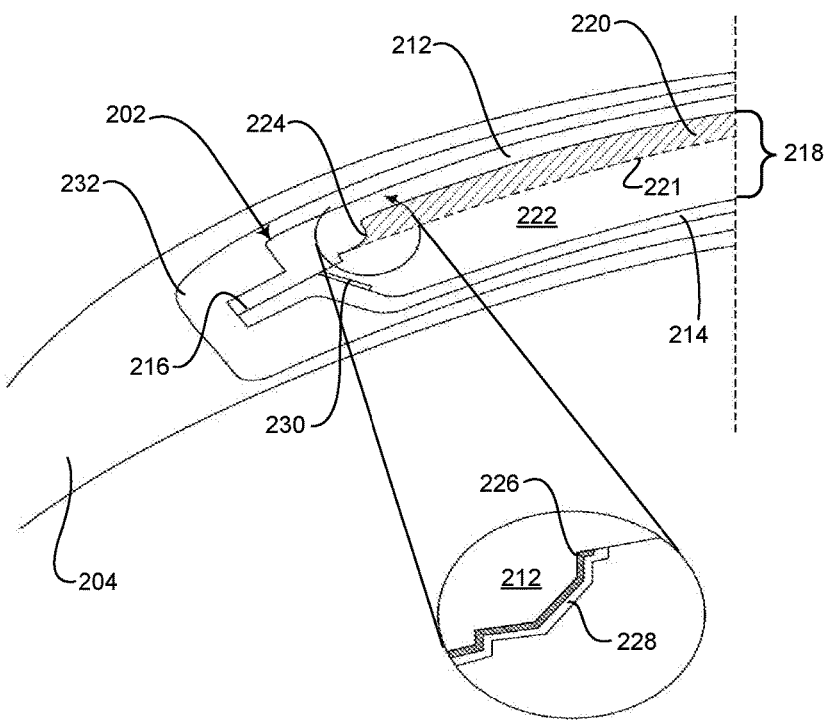

FIGS. 2A-2B together illustrate an embodiment of an electrowetting gas-permeable contact lens 200 including an electrowetting cell 202. FIG. 2A is a plan view, FIG. 2B a cross-sectional view taken substantially along section line B-B in FIG. 2A. Electrowetting cell 202 is centrally positioned within contact lens material 204. Control electronics 206 can be disposed in or on contact lens material 204. In some embodiments, control electronics 206 can include control logic, one or more power supplies (e.g., batteries and/or super capacitors), and communication electronics. An antenna 210, which can perform some of all of the functions described in connection with antenna 140, can be coupled to control electronics 206, for instance to allow for communication via the communication electronics or energy harvesting for an internal battery or capacitor.

Control electronics 206 choreograph the operation of electrowetting cell 202, for example by determining when to cause the electrowetting cell to provide accommodation and by how much. In one embodiment, control electronics 206 can perform some or all the functions described above in connection with power supply 120 and its components, controller 125 and its components, and sensor system 135. For example, control electronics 206 may establish a potential difference between oil electrode 224 and the saline electrode 230 (see below), which can cause the oil-saline interface 221 to change shape to provide a change in optical power. Control electronics 206 can be coupled to oil electrode 224 and saline electrode 230 by interconnect 208, which can be a wired or wireless interconnect, for example. Interconnect 208 may be disposed on one or more surfaces of contact lens material 204 that separate the control electronics 206 from the oil and saline electrodes.

As shown in FIG. 2B, electrowetting cell or lens 202 includes two optical windows 212 and 214. In a central region of lens 202, optical windows 212 and 214 are spaced apart to form a sealed enclosure 218 within which the immiscible fluids used in the electrowetting cell—oil 220 and saline solution 222 in this embodiment—are held. Optical windows 212 and 214 are joined around their perimeters at a sealing region 216, so that they seal enclosure 218 to minimize or prevent oil 220 and saline 222 from leaking. In different embodiments, optical windows 212 and 214 can be planar optics or curved optics with focal power. In some embodiments, at least one of optical windows 212 and 214 can include a geometric feature useful for the deposition of an electrode and a dielectric for the electrowetting surface of the device.

Optical windows used in traditional electrowetting lenses are comprised of gas-impermeable materials, but in electrowetting cell 202 optical windows 212 and 214 incorporate rigid gas-permeable plastic elements as one or more of the optics. Technically speaking, nearly all plastics are finitely permeable to most gases, including oxygen, but the flux of gas through most polymer materials is too low to be of practical benefit in a contact lens application. To truly be considered gas-permeable for contact lens applications, the material must have a gas permeability of 20 Barrer or more. The Barrer is a non-SI unit of gas permeability used in the membrane technology and contact lens industry, and is defined as:

$$1 \text{ Barrer} = 10^{-10} \frac{\text{cm}^3_{STP} \cdot \text{cm}}{\text{cm}^2 \cdot \text{s} \cdot \text{cmHg}}$$

Where "$\text{cm}^3_{STP}$" is standard cubic centimeter, which is a unit of amount of gas rather than a unit of volume; it represents the amount of gas molecules or moles that would occupy one cubic centimeter at standard temperature and pressure (STP), as calculated using the ideal gas law. The "cm" corresponds to the thickness of the material whose permeability is being evaluated, "$\text{cm}^3_{STP} \text{ cm}^{-2} \text{ s}^{-1}$" to the flux of gas through the material, and "cmHg" to the pressure drop across the material. That is, the Barrer unit measures the rate of fluid flow passing through an area of material with a given thickness driven by a given pressure. In SI units, one Barrer is equivalent to $3.34\text{E-}16 \text{ mol Pa}^{-1} \text{ s}^{-1} \text{ m}^{-1}$.

Rigid gas-permeable contact lens materials of many formulations can be used for optical windows 212 and 214 and can have oxygen permeability values exceeding 100 Barrer, which provides a highly-permeable material. These materials are produced by manufacturers in a "button" format consisting of a small cylindrical plug of material that can be machined using specialized lathing equipment, for example single-point diamond turning machines such as those produced by DAC International, Inc. (http://www.dac-intl.com/). Although it is possible to machine a rigid gas-permeable optical element for use in the disclosed embodiments, cast molding the rigid gas-permeable elements, such as optical windows 212 and 214 and possibly other elements of electrowetting cell 202, can be more cost-effective, leading to scalability for high-volume manufacturing. Thus, any of the described embodiments can incorporate rigid gas-permeable plastic elements that are produced by either lathe turning or cast molding, but it is possible that new materials could be developed that could be directly injection molded.

Sealing region 216 can also be made gas-permeable in some embodiments. In an embodiment where optical windows 212 and 214 are gas-permeable, sealing region 216 can be formed by crimping, but in other embodiments the rigid gas-permeable elements used for optical windows 212 and 214 can incorporate geometric features that facilitate their mating and assembly to fine tolerances in sealing region 216. In this way features useful for sealing, or for locating seals, or for providing sealing surfaces can be directly incorporated in one or more of the optical gas-permeable elements. In still other embodiments, the outer edges of optical windows 212 and 214—that is, the edges closest to the outer edges of contact lens material 204—can be contoured to avoid sharp features that may be uncomfortable or may otherwise complicate other aspects of incorporating a gas-permeable electrowetting cell into a contact lens form factor. For example, in some embodiments electrowetting cell 202 can be overmolded or encased in one or more biocompatible soft materials. These soft materials may be damaged by sharp edges of rigid elements during processing and/or handling, leading to lower manufacturing yields and/or product failure in the field.

Sealing region 216 can also be formed using gas-permeable sealing materials with appreciable oxygen permeability to join optical windows 212 and 214, but if the dimensions of sealing region 216 are small, oxygen-impermeable sealing materials can be used without significantly impacting overall oxygen permeability of the assembly. If used, sealing materials with an oxygen permeability greater than about 30 Barrer are preferred. Specific oxygen-permeable sealing material examples can include silicone pressure sensitive adhesives, or other silicone-containing materials such as two-part Pt cure silicones, RTV moisture-cure silicones, UV-curable silicones, and the like. Custom polymerizable silicone- and/or fluorine-containing formulations can also be used without limitation.

Within sealed enclosure 218 are two immiscible liquids. In the illustrated embodiment, the two liquids are an oil and a saline solution, but they can be different liquids in other embodiments. Because they are immiscible, the two liquids do not mix but instead separate into two layers: an oil layer 220 and a saline layer 222. Oil layer 220 is in contact with optical window 212, saline layer 222 is in contact with optical window 214, and the oil and saline layers are in contact with each other along a fluid interface 221. When an electric field is applied to one or both of oil layer 220 and saline layer 222, the shape of fluid interface 221 changes, thus changing the optical properties, such as magnification, of electrowetting cell 202.

In one embodiment, oil layer 220 can be a gas-permeable fluid. Examples of gas-permeable fluids that can be used in embodiments of oil layer 220 include one or more of: a siloxane fluid, a phenylsiloxane fluid, a fluorocarbon fluid, a partially-fluorinated alkane fluid, an alicyclic fluid, a germane fluid, or any other fluid formulation that has an oxygen permeability greater than about 30 Barrer.

For saline layer 222, typical saline solutions can have a reasonably high oxygen permeability. For instance, in some embodiments saline solutions with an oxygen permeability greater than about 50 Barrer can be used, although there is some latitude for using a lower permeability, thereby permitting latitude in the saline formulation, but not to the extent that oxygen permeability is significantly impacted. Existing saline solutions used in electrowetting cells could already have acceptable gas permeability properties, but it is possible, due to various formulation embodiments, that component additions to saline solution may lower the gas permeability of the saline phase. An exemplary saline solution may comprise only a salt and water—for example, physiological saline solution.

For electrowetting cell 202 to function, there must be an electrowetting dielectric surface for each fluid in the cell. This surface is commonly referred to as "the electrode" and is used to apply an electric field across its respective liquid layer. Each liquid layer within sealed enclosure 218 is in contact with its own electrode: oil layer 220 is in contact with electrode 224, which is formed on an angled surface of optical window 212 around the perimeter of sealed enclosure 218, and saline layer 222 is in contact with electrode 230, which is formed on an angled surface of optical window 214 around the perimeter of sealed enclosure 218. In embodiments of an electrowetting cell one electrode can include a conductive layer that is insulated from its respective liquid by a dielectric layer, while the other electrode can include a conductive layer that is either completely uninsulated or only partially insulated by a dielectric. In the illustrated embodiment, oil electrode 224 is insulated and saline electrode 230 is uninsulated, but other embodiments could have the opposite arrangement; thus, embodiments described as the oil electrode could be used as the saline electrode in other embodiments, and embodiments described as the saline electrode could be used as the oil electrode in other embodiments.

In the illustrated embodiment both electrodes 224 and 230 include a conductive layer positioned on the respective optical window, and oil electrode 224 also includes a dielectric layer formed over its conductive layer (see inset). For instance, as shown in the enlargement of oil electrode 224, the oil electrode includes a conductive layer 226 formed on optical window 212, and a dielectric layer 228 formed on conductive layer 226. Saline electrode 230 can have a structure similar to electrode 224, but it need not have the same shape and can be without a dielectric layer or can be only partially covered by a dielectric layer.

A problem with conductors used in existing designs is that they are metals, which are substantially impermeable save for defects inherent in the deposited films. In some embodiment of electrowetting cell 202, gas-impermeable electrodes can be acceptable if they occupy a small enough area that they don't significantly impact the gas permeability of the whole cell; in these embodiments metal conductors can be used, and in some embodiments multiple conductors can be used, for instance a titanium or chromium adhesion layer topped with a thin film of gold. But in other embodiments of electrowetting cell 202, the conductor used in one or both of electrodes 224 and 230 can be of a substantially oxygen-permeable material and/or oxygen-permeable geometric design. In other embodiments, in one or both of the oil and saline electrodes the conductor can comprise a substantially gas-permeable conducting polymer, such as a polyacetylene.

In one embodiment, dielectric 228 used in electrode 224 comprises a gas-permeable polymer, for example silicone elastomer and/or Teflon AF. Custom formulations of polymerizable or otherwise coatable dielectrics are anticipated. Dielectrics having a gas permeability of greater than 30 Barrer are preferred. In another embodiment the dielectric is not substantially gas-permeable, but its coverage is instead limited to just a small area disposed over the conductor and a small margin around the conductor to ensure adequate coverage. This can be achieved by masked deposition of the dielectric or by selective removal of the dielectric (by laser ablation, plasma etching, machining, etc.). In this manner, gas permeability of the overall electrowetting cell constructed with other gas-permeable components may be, on average, high, but the small area covered by the dielectric may be low. Various other dielectrics can be used, for example parylene and a fluorocarbon top coat such as Teflon AF 1600.

Electrowetting cell 202 is surrounded by a protective coating 232, which in an embodiment can include one or more protective and/or biocompatible coatings. The coatings can serve multiple functions, such as secondary adhesion and/or sealing of the structure, providing optical effects (refractive), protecting exposed electrical interconnects, improving surface contours and/or form, or other functions. In another embodiment, protective coating 232 can comprise a silicone elastomer, which is highly gas-permeable. In yet another embodiment protective coating 232 can include a gas-permeable, index-matching resin composition that hides internal structural elements of the electrowetting cell. And in another embodiment protective coating 232 can comprise a polymerizable, rigid gas-permeable contact lens material having an oxygen permeability greater than about 30 Barrer.

The encapsulated gas-permeable electrowetting cell 202, including its gas-permeable protective coating 232, is embedded into a highly oxygen-permeable silicone hydrogel soft contact lens material 204 (e.g., delefilcon a, lotrafilcon a, lotrafilcon b, etc.). In some cases, interfacial adhesion between the silicone hydrogel material and the underlying protective gas-permeable coating may be sufficient that no special steps are required. In other cases, a surface treatment may be preferentially applied to the gas-permeable protective coating. Applicable surface treatments may include the use of corona or plasma treatments, atmospheric plasma treatments, solvent wipes or dips, primer application, organosilane deposition, or other surface chemical reactions that may impart improved adhesion. The foregoing surface treatment methods may also be applied to the gas-permeable electrowetting cell prior to application of the protective coating 232 to improve interfacial bonding at that interface.

FIG. 3 illustrates another embodiment of an oil electrode 300. As with electrode 224, oil electrode 300 includes a conductive layer 302 formed on optical window 212 and a dielectric layer 304 formed over conductive layer 302. The primary difference between oil electrode 300 and oil electrode 224 is in the construction of conductive layer 302. Conductive layer 302 can be formed of a deposited layer of overlapping silver nanowires, which features an open, porous network structure and high conductivity. In the illustrated embodiment a separate gas-permeable dielectric layer 304 is formed over conductive layer 302 as shown, but in other embodiments the silver nanowires can be embedded in a dielectric.

FIGS. 4A-4B together illustrate yet another embodiment of an oil electrode 400. As with electrode 224, oil electrode 400 includes a conductive layer 402 formed on optical window 212 and a dielectric layer 406 formed over conductive layer 402. The primary difference between oil electrode 400 and oil electrode 224 is in the construction of conductive layer 402. In the illustrated embodiment, conductive layer 402 can be formed of a non-gas-permeable material such as a metal or conductive non-metal, or can be formed from a gas-permeable material. Either way, to improve its gas permeability conductive layer 402 is perforated with a plurality of structured openings 404 that extend through the thickness of the conductive layer, so that the surface of optical window 212, which is itself gas permeable, is exposed where the structured openings are located. Conductive layer 402 is then covered with a gas-permeable dielectric layer 406, which fills structured openings 404 and overlays the rest of conductive layer 402. Dielectric layer 406 has an overall thickness h. In one embodiment, conductive layer 402 can be a thin film metal that is patterned by any convenient means (photolithography, laser ablation, etc.) to create a porous mesh or grid type structure, thereby forming openings that permit gas transport.

FIG. 4B illustrates a plan view of embodiments of structured openings 404 in conductive layer 402. The individual structured openings 404 can have any shape; in the illustrated embodiment structured openings 404 are square or round, but in other embodiments they can have other shapes. Moreover, in any given embodiment all the structured openings need not have the same shape. Each structured opening 404 has a maximum dimension: for a square opening 404 the maximum transverse dimension might be its diagonal dimension W, while for a round opening 404 the maximum transverse dimension can be its diameter D. Generally, it is desirable that the maximum size of the structured openings is small relative to the overall thickness of the applied dielectric; in other words, it is desirable to keep the ratio of the maximum transverse dimension (e.g., W or D) and the dielectric thickness (e.g., h) below a selected number. For example, if a 4 micron dielectric (e.g., h=4 microns) is used, then the maximum opening size (e.g., W or D) may be about 0.4 microns, for a W/h or D/h ratio of about 0.1. Of course, in other embodiments the W/h or D/h ratio can be higher or lower; in other embodiments, for instance, the ratio could any value between 0.01 and 1.0. Moreover, the practical limit of the ratio can be determined by experimentation and acceptable lens performance.

Figure 5:
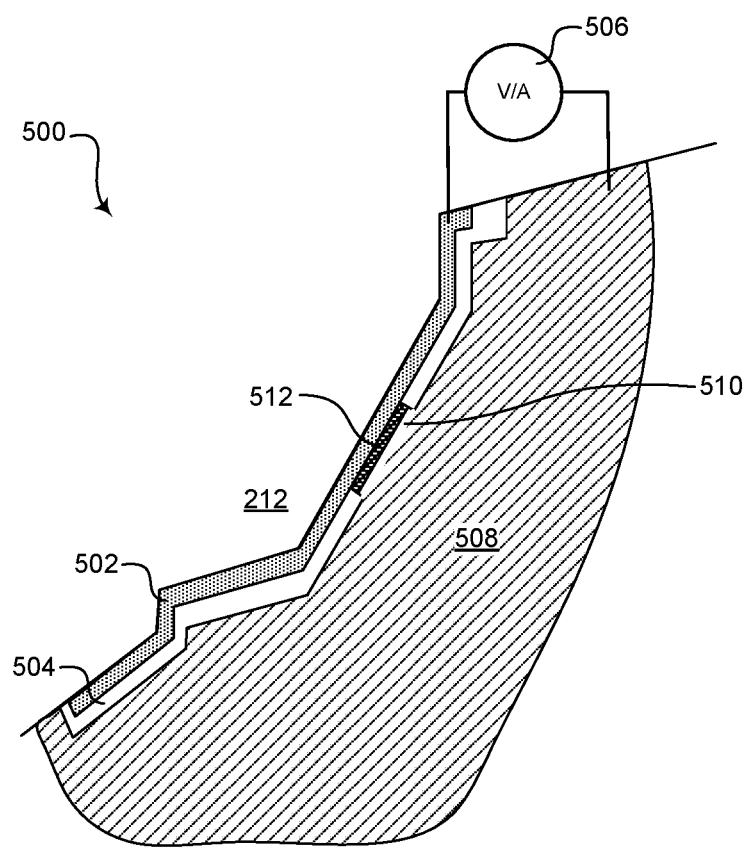
FIG. 5 illustrates another embodiment of an oil electrode of the electrowetting cell.

FIG. 5 illustrates another embodiment of an oil electrode 500. It is generally desirable to have the electrowetting dielectric be as free of defects as possible, so oil electrode 500 is an example of a "self-healing" electrode that can automatically repair dielectric damage. Oil electrode 500 includes a conductive layer 502 formed on optical window 212, and a dielectric layer 504 is formed over conductive layer 502 so that the conductive layer is sandwiched between optical window 212 and dielectric layer 504. An AC or DC voltage and/or current source 506 is electrically coupled to conductive layer 502 and to liquid layer 508, which in this case is the oil layer; typically the positive terminal of source 506 will be coupled to the liquid layer 508 and the negative terminal will be coupled to conductive layer 502.

Defects in dielectric layer 504, such as hole or void 510, can occur for various reasons. They can be present from the beginning, for example due to material defects or manufacturing defects, or can appear over time due to electrical cycling, exposure to fluid 508, and so on. If the defects are significant enough to expose conductive layer 502 directly to fluid 508, voltages applied to the conductive layer during operation of the electrowetting cell can cause electrolysis of fluid 508. But by careful selection of materials for conductive layer 502, dielectric 504, and fluid 508, the application of an AC or DC voltage and/or current by source 506 will cause dielectric layer 504 to "self-heal" by causing fast electrolytic growth of a dielectric layer 512 on the portion of conductive layer 502 in hole or void 510, so that conductive layer 502 is once again electrically insulated from fluid 508 and cannot electrolyze the fluid.

In an embodiment, conductive layer 502 can be a "valve metal"—that is, a metal that forms an oxide when used as an anode in an electrolytic cell. Valve metals include magnesium, aluminum, titanium, vanadium, chromium, zinc, zirconium, niobium, antimony, hafnium, tantalum, tungsten, and bismuth. In an embodiment, liquid 508 can be a solution including a solvent in which an electrolyte is dissolved; the electrolyte is a chemical compound, such as a salt, an acid, or a base, that dissociates into ions when dissolved in the solvent, making liquid 508 an ionic electrical conductor. Examples of materials that can be used for dielectric layer 504 include metal oxides, Teflon AF, and parylene.

Figure 6:
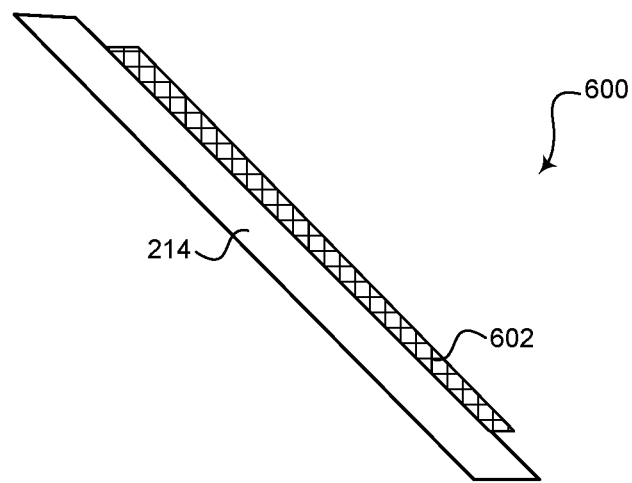
FIG. 6 illustrates an embodiment of a saline electrode of the electrowetting cell.

FIG. 6 illustrates another embodiment of a saline electrode 600. As with electrode 230, saline electrode 600 includes a conductive layer 602 formed on optical window 214. The primary difference between saline electrode 600 and saline electrode 230 is in the construction of conductive layer 602. In one embodiment, an indium tin oxide layer, which functions as the saline-contacting electrode, can be deposited on the optical layer 214, but the low permeability of indium tin oxide makes this is undesirable from an oxygen permeability standpoint. In another embodiment, saline electrode 600 can be a small metallized area that does not appreciably block gas permeability of the overall assembly. In another embodiment, this may be a small metallized area deposited directly on a portion of the dielectric. In another embodiment, saline electrode 602 can comprise silver nanowires, optionally with a binding, film-forming polymer. In essence, any saline-contacting electrode that does not appreciably block direct oxygen transport through the electrowetting cell assembly may be implemented without limitation.

Figure 7:
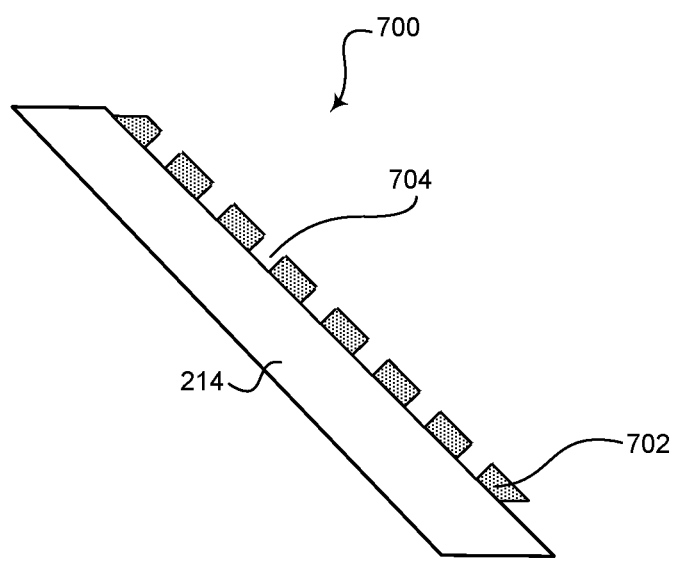
FIG. 7 illustrates another embodiment of a saline electrode of the electrowetting cell.

FIG. 7 illustrates another embodiment of a saline electrode 500. As with saline electrode 230, saline electrode 700 includes a conductive layer 702 formed on optical window 214. The primary difference between saline electrode 700 and saline electrode 230 is in the construction of conductive layer 702. In the illustrated embodiment, conductive layer 702 can be formed of a non-gas-permeable material such as a metal or conductive non-metal, or can be formed from a gas-permeable material. Either way, to improve its permeability, conductive layer 702 is perforated with a plurality of structured openings 704 that extend through the thickness of the conductive layer, so that the surface of optical window 214 is exposed where the structured openings are located. Saline electrode 700 is therefore somewhat analogous to oil electrode 400, described above but without a dielectric layer, although in some embodiments conductive layer 702 can be partially covered by a dielectric layer.

The above description of embodiments, including what is described in the abstract, is not intended to be exhaustive or to limit the invention to the described forms. Specific embodiments of, and examples for, the invention are described herein for illustrative purposes, but various equivalent modifications are possible within the scope of the invention in light of the above detailed description, as those skilled in the relevant art will recognize.

The terms used in the following claims should not be interpreted to limit the invention to the specific embodiments disclosed in the specification and the claims. Rather, the scope of the invention is to be determined entirely by the following claims, which are to be interpreted using established claim interpretation doctrines.

The invention claimed is:

1. An electrowetting contact lens comprising:
    an electrowetting cell comprising:
        first and second optical windows, each having an inside surface and an outside surface and joined around their perimeter to form a sealed enclosure between the inside surfaces of the first and second optical windows,
        a first gas-permeable electrode formed on the first optical window, the first gas-permeable electrode comprising an electrically conductive layer and at least one dielectric layer, the electrically conductive layer being sandwiched between the first optical window and the at least one dielectric layer,
        a second gas-permeable electrode formed on the second optical window, the second gas-permeable electrode comprising an electrically conductive layer,
        an oil layer positioned in the sealed enclosure so that the oil layer is in contact with the inner surface of the first optical window and with the first gas-permeable electrode, and
        a saline solution layer positioned in the sealed enclosure so that the saline solution layer is in contact with the oil layer, with the inner surface of the second optical window, and with the second gas-permeable electrode,
    a protective coating surrounding and completely enclosing the electrowetting cell; and
    a contact lens material, distinct from the protective coating, surrounding and completely enclosing the protective coating.

2. The contact lens of claim 1 wherein the conductive layer of at least one of the first and second gas-permeable electrodes is perforated with a plurality of structured openings.

3. The contact lens of claim 2 wherein the size of the structured openings is small relative to the overall thickness of the dielectric layer.

4. The contact lens of claim 3 wherein the dielectric layer has a thickness of 4 microns and the structured openings have a maximum dimension of 0.4 microns.

5. The contact lens of claim 1 wherein the first and second gas-permeable electrodes comprise a mesh of nanowires.

6. The contact lens of claim 1 wherein at least one of the first and second optical windows, the contact lens material, and the protective coating are gas-permeable.

7. The contact lens of claim 6 wherein:
    if gas-permeable, the first and second optical windows have a gas permeability greater than or equal to 100 Barrer;
    if gas-permeable, the oil layer has a gas permeability greater than or equal to 30 Barrer;
    if gas-permeable, the saline solution layer has a gas permeability greater than or equal to 50 Barrer;
    if gas-permeable, the protective coating has a gas permeability greater than or equal to 30 Barrer; and
    if gas-permeable, the contact lens material has a gas permeability greater than or equal to 100 Barrer.

8. The contact lens of claim 1 wherein the dielectric layers of the first and second gas-permeable electrodes have a gas permeability greater than or equal to 30 Barrer.

9. The contact lens of claim 1 wherein the first and second optical windows are joined along a sealing region around their perimeters using a sealing material having a gas permeability greater than or equal to 30 Barrer.

10. The device of claim 1 wherein the size of the structured openings is small relative to the overall thickness of the dielectric layer.

11. The device of claim 10 wherein the dielectric layer has a thickness of 4 microns and the structured openings have a maximum dimension of 0.4 microns.

12. An eye-mountable accommodation device comprising:
    an electrowetting cell comprising:
        first and second optical windows, each having an inside surface and an outside surface and joined around their perimeter to form a sealed enclosure between the inside surfaces of the first and second optical windows,
        a first gas-permeable electrode formed on the first optical window, the first gas-permeable electrode comprising an electrically conductive layer and at least one dielectric layer, the electrically conductive layer being sandwiched between the first optical window and the at least one dielectric layer,
        a second gas-permeable electrode formed on the second optical window, the second gas-permeable electrode comprising an electrically conductive layer,
        an oil layer positioned in the sealed enclosure so that the oil is in contact with the inner surface of the first optical window and with the first gas-permeable electrode, and
        a saline solution layer positioned in the sealed enclosure so that the saline solution is in contact with the oil layer, with the inner surface of the second optical window, and with the second gas-permeable electrode,
    a protective coating surrounding and completely enclosing the electrowetting cell;
    a contact lens material, distinct from the protective coating, surrounding and completely enclosing the protective coating; and
    control electronics mounted on the contact lens material and electrically coupled to the first and second gas-permeable electrodes.

13. The device of claim 12 wherein the conductive layer of at least one of the first and second gas-permeable electrodes is perforated with a plurality of structured openings.

14. The device of claim 12 wherein the first and second gas-permeable electrodes comprise a mesh of nanowires.

15. The device of claim 12 wherein at least one of the first and second optical windows, the contact lens material, and the protective coating are gas-permeable.

16. The device of claim 15 wherein:
if gas-permeable, the first and second optical windows have a gas permeability greater than or equal to 100 Barrer;
if gas-permeable, the oil layer has a gas permeability greater than or equal to 30 Barrer;
if gas-permeable, the saline solution layer has a gas permeability greater than or equal to 50 Barrer;
if gas-permeable, the protective coating has a gas permeability greater than or equal to 30 Barrer; and
if gas-permeable, the contact lens material has a gas permeability greater than or equal to 100 Barrer.

17. The device of claim 12 wherein the dielectric layers of the first and second gas-permeable electrodes have a gas permeability greater than or equal to 30 Barrer.

18. The device of claim 12 wherein the first and second optical windows are joined along a sealing region around their perimeters using a sealing material having a gas permeability greater than or equal to 30 Barrer.

19. The device of claim 12, further comprising an antenna coupled to the control electronics.

20. The device of claim 12 wherein the control electronics include a battery or a capacitor.

21. An electrowetting contact lens comprising:
an electrowetting cell comprising:
   first and second optical windows, each having an inside surface and an outside surface and joined around their perimeter to form a sealed enclosure between the inside surfaces of the first and second optical windows,
   a first electrode formed on the first optical window, the first electrode comprising an electrically conductive layer and at least one dielectric layer, the electrically conductive layer being sandwiched between the first optical window and the at least one dielectric layer,
   a second electrode formed on the second optical window, the second electrode comprising an electrically conductive layer,
   an oil layer positioned in the sealed enclosure so that the oil is in contact with the inner surface of the first optical window and with the first electrode, and
   a saline solution layer positioned in the sealed enclosure so that the saline solution is in contact with the oil layer, with the inner surface of the second optical window, and with the second electrode,
a protective coating surrounding and completely enclosing the electrowetting cell; and
a contact lens material, distinct from the protective coating, surrounding and completely enclosing the protective coating,
wherein at least one of the first and second optical windows, the contact lens material, and the protective coating is gas-permeable.

22. The contact lens of claim 21 wherein the conductive layer of at least one of the first and second electrodes is perforated with a plurality of structured openings.

23. The contact lens of claim 22 wherein the size of the structured openings is small relative to the overall thickness of the dielectric layer.

24. The contact lens of claim 23 wherein the dielectric layer has a thickness of 4 microns and the structured openings have a maximum dimension of 0.4 microns.

25. The contact lens of claim 21 wherein the first and second electrodes comprise a mesh of nanowires.

26. The contact lens of claim 21 wherein:
if gas-permeable, the first and second optical windows have a gas permeability greater than or equal to 100 Barrer;
if gas-permeable, the oil layer has a gas permeability greater than or equal to 30 Barrer;
if gas-permeable, the saline solution layer has a gas permeability greater than or equal to 50 Barrer;
if gas-permeable, the protective coating has a gas permeability greater than or equal to 30 Barrer;
if gas-permeable, the contact lens material has a gas permeability greater than or equal to 100 Barrer.

27. The contact lens of claim 21 wherein the dielectric layer of the first electrode has a gas permeability greater than or equal to 30 Barrer.

28. The contact lens of claim 21 wherein the first and second optical windows are joined along a sealing region around their perimeters using a sealing material having a gas permeability greater than or equal to 30 Barrer.

29. The contact lens of claim 21 wherein the oil layer is an electrolytic solution and the first electrode is a self-healing electrode comprising:
a conductive layer made of a valve metal;
a dielectric layer formed over the conductive layer; and
an AC or DC voltage or current source electrically coupled to the conductive layer and to the oil layer.

* * * * *